United States Patent [19]
Nakayama et al.

[11] Patent Number: 5,453,246
[45] Date of Patent: Sep. 26, 1995

[54] DISPENSING APPARATUS

[75] Inventors: Naoki Nakayama, Wako; Akio Akiyama, Tokyo; Takayuki Ushida, Tokyo; Hiroshi Takao, Tokyo, all of Japan

[73] Assignees: Mitsubishi Yuka Bio-Clinical Laboratories, Inc., Tokyo; Daisen Sangyo Co., Ltd., Osaka; Tafuto Co., Ltd., Tokyo, all of Japan

[21] Appl. No.: 254,775

[22] Filed: Jun. 6, 1994

Related U.S. Application Data

[63] Continuation-in-part of Ser. No. 118,328, Sep. 9, 1993, abandoned.

[30] Foreign Application Priority Data

Sep. 18, 1992 [JP] Japan ..................... 4-249881
Mar. 24, 1994 [JP] Japan ..................... 6-053638

[51] Int. Cl.⁶ ..................................... G01N 35/10
[52] U.S. Cl. .................. 422/63; 422/62; 422/100; 422/104; 73/864.11; 73/864.14; 73/864.24; 73/864.25; 141/130; 436/174; 436/180
[58] Field of Search ................ 422/100–104, 422/63, 62, 65, 67, 105; 436/43, 47, 49, 50, 54, 55, 180; 73/864.25, 864.24, 864.14, 864.11; 83/949; 141/121, 123, 130, 248

[56] References Cited

U.S. PATENT DOCUMENTS

| | | | |
|---|---|---|---|
| 3,376,751 | 4/1968 | Jungner | 73/864.24 |
| 3,736,099 | 5/1973 | Begg et al. | 422/100 |
| 3,768,978 | 10/1973 | Grubb et al. | 422/100 |
| 3,786,683 | 1/1974 | Berman et al. | 73/425.4 |
| 3,888,125 | 6/1975 | Mochida | 73/423 A |
| 4,184,815 | 1/1980 | Cassor et al. | 417/477 |
| 4,210,026 | 7/1980 | Amos et al. | 73/425.6 |
| 4,294,802 | 10/1981 | Johansson | 422/103 |
| 4,298,570 | 11/1981 | Lillig et al. | 422/64 |
| 4,311,667 | 1/1982 | Gocho | 422/64 |
| 4,448,752 | 5/1984 | Banno et al. | 422/81 |
| 4,728,501 | 3/1988 | Atake | 422/100 |
| 5,085,345 | 2/1992 | Wells | 222/95 |
| 5,114,679 | 5/1992 | Reifler et al. | 422/100 |
| 5,318,413 | 6/1994 | Bertoncini | 417/475 |
| 5,365,798 | 11/1994 | Kressirer | 73/864.11 |

FOREIGN PATENT DOCUMENTS

| | | |
|---|---|---|
| 0182943 | 4/1986 | European Pat. Off. . |
| 0283614 | 9/1988 | European Pat. Off. . |
| 2447751 | 8/1980 | France . |
| 2553151 | 4/1985 | France . |
| 1141800 | 1/1969 | United Kingdom . |
| WO88/08985 | 11/1988 | WIPO . |

*Primary Examiner*—James C. Housel
*Assistant Examiner*—Long V. Le
*Attorney, Agent, or Firm*—Oblon, Spivak, McClelland, Maier & Neustadt

[57] ABSTRACT

A dispensing apparatus includes a tube-feeding portion which holds and feeds a tube made of an elastic material, a tube nozzle portion which supports an end portion of the tube and guides the tube to a liquid container by moving the tube up and down and from side to side, a tube-pressing and conveying portion provided between the above tube-feeding portion and the tube nozzle portion which draws out the tube from the tube-feeding portion, presses the tube and conveys the tube to the tube nozzle portion and a tube end-discarding portion, wherein the tube-pressing and conveying portion includes tube-pressing rollers which press the tube and set a length of a tube-pressing portion.

6 Claims, 5 Drawing Sheets

A - A' Sectional View 5,453,246

DISPENSING APPARATUS

This is a continuation-in-part application of U.S. Ser. No. 08/118,328 filed Sep. 9, 1993 and abandoned on Mar. 6, 1994.

BACKGROUND OF THE INVENTION

1. Field of the Invention

This invention relates to a liquid-dispensing apparatus which can be applied to handling of a liquid for research, development, production and inspection in science and engineering, medical science and production techniques.

2. Discussion of the Background

As one example of a conventional apparatus, a partially improved apparatus of the apparatus disclosed in Japanese Provisional Patent Publication No. 102151/1994 (U.S. patent application Ser. No. 08/118,328), which is a previous invention by the present inventors, is shown in FIG. 5 and FIG. 6.

In a conventional liquid-dispensing apparatus which is used for clinical tests, in order to prevent contamination between samples to be tested, a sampling chip which is not contaminated with a previous sample is required to be used for each dispension. Accordingly, a sampling chip such as a plastic molded product prepared by injection molding has been generally used, but such a sampling chip is extremely expensive.

As a sample-sucking mechanism, there may be mostly used a mechanism using a cylinder. An apparatus using such a mechanism is expensive and it is necessary to fit the above sampling chip to a nozzle at the end of a cylinder each time. When a liquid is sucked by a cylinder, even a slight failure of fitting causes leakage of air at a fitting portion so that there are drawbacks in that a reduced pressure state may not be maintained and inaccuracy in the amount sucked will occur.

In a roller system previously proposed by the present inventors as an improvement of such a sample-sucking mechanism, as shown in FIG. 5 and FIG. 6 which is a sectional view of FIG. 5 cut along with A–A' line, a pressing roller 50 is driven by a driving portion not shown in the figure, and a moving amount of the pressing roller 50 with a pinion 52 which moves while rotating determines a sample-sucking amount. The length of a rack 51 is required to have a length at least equal to a length of pressing a tube+α, whereby it is difficult to miniaturize the whole structure.

That is, the rack 51 and the pinion 52 are provided in order to prevent the tube 2 from being pulled by the pressing roller 50 and slipped greatly when the pressing roller 50 rotates while pressing a tube 2. When the pressing roller 50 is moved, the pinion 52 provided on the same axis of the pressing roller 50 is rotated by the rack 51 so that the pressing roller 50 is also rotated, whereby almost no slippage of the tube is caused.

However, in such a system, a thickness of the tube 2 pressed by pressing actually causes a difference of a pitch circle. Therefore, when the pressing roller 50 moves while pressing the tube 2, the tube 2 slightly slips, whereby an adverse influence an conveying occurs. For this reason, a tube having a different wall thickness cannot be used.

SUMMARY OF THE INVENTION

An object of the present invention is to provide an improved dispensing apparatus in which a roller system is used as further improvement of a sample-sucking mechanism, but the drawback of the roller system is removed so that the tube does not slip so therefore improve dispensing precision.

The present invention is directed to a dispensing apparatus which comprises:

a tube-feeding portion A which holds and feeds a tube 2 made of an elastic material, a tube nozzle portion B which supports an end portion of the above tube 2 and guides it to a liquid container 14 by moving it up and down and from side to side, a tube-pressing and conveying portion C provided between the tube-feeding portion A and the tube nozzle portion B, which draws out the above tube 2 selectively from the above tube-feeding portion A, presses it selectively and conveys it selectively to the above tube nozzle portion B and a tube end-discarding portion D, wherein the above tube-pressing and conveying portion C comprises tube-pressing rollers 5 which can press the tube 2 selectively and set the length of a tube-pressing portion selectively.

Further, the above tube-pressing and conveying portion C comprises a pressing amount-setting means 22 which can change a tube-pressing portion set amount by the above tube-pressing rollers 5, in response to a control signal.

The above tube-pressing rollers 5 comprise a pair of engaged rollers having substantially the same diameter.

The above tube-pressing and conveying portion C further comprises at least one dancer roller 6 which absorbs a change of a tube-conveying length by changing its tube-supporting position so as not to change a tube end position in the above tube nozzle portion B when a tube-pressing portion set amount is changed by the above tube-pressing rollers 5.

DESCRIPTION OF THE PREFERRED EMBODIMENTS

Figure 1:
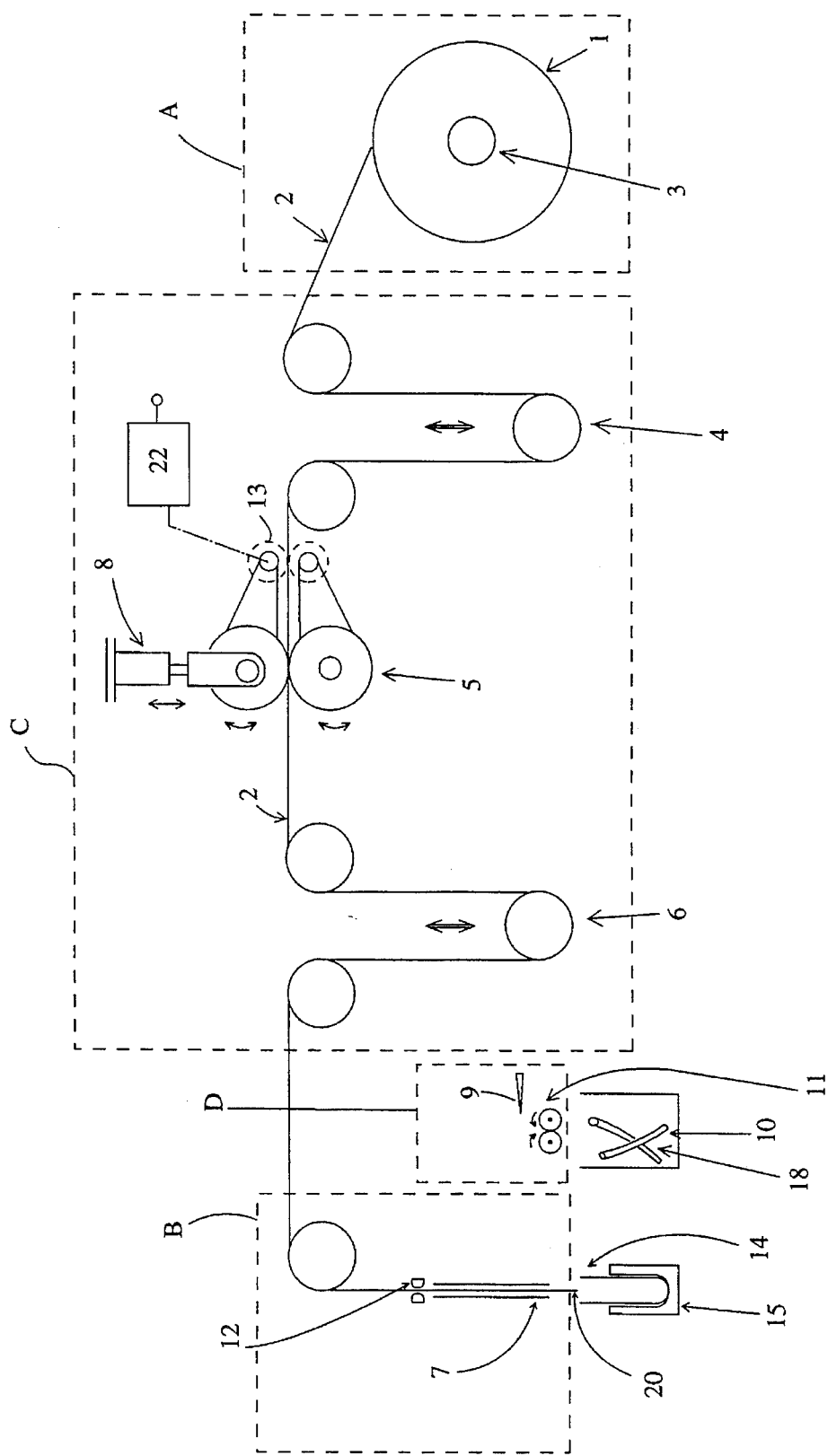
FIG. 1 is a view showing an embodiment of the dispensing apparatus of the present invention.

FIG. 1 is a view showing a constitution of one example of the dispensing apparatus according to the present invention, which comprises a tube-feeding portion A, a tube nozzle portion B, a tube-pressing and conveying portion C provided between the above tube-feeding portion A and the above tube nozzle portion B and tube end-discarding portion D.

A tube 2 wound around a reel 1 in the tube-feeding portion A is drawn out from a tube-feeding axis 3 and then introduced to a nozzle 7 in the tube nozzle portion B through a dancer roller 4 which maintains tension of the tube 2 constantly, tube-pressing rollers (nip rollers) 5 and a dancer roller 6 which absorbs a change of a tube-conveying length so as not to change a tube end position of the tube 2 caused by pressing, all of which are provided in the tube-pressing and conveying portion C.

The tube 2 to be used in the present invention may be any tube having such elasticity that it can be choked by applying pressure from outside and can be substantially recovered by removing pressure, and a material and a preparation method thereof are not limited. For example, a vinyl tube prepared by extrusion molding may be used.

The tube used in Example was a transparent vinyl tube having a diameter of 2 mm and a wall thickness of 0.5 mm, but the tube of the present invention is not limited thereby. The diameter may be suitably selected depending on the size of an inlet opening of a liquid container to be used. The wall thickness may be suitably selected depending on a diameter, a material, easiness of choking when pressure is applied and recovery when pressure is removed.

The tube-pressing rollers 5 are a pair of engaged rollers having substantially the same diameter. The engaged rollers are preferably the so-called nip rollers which rotate while engaging with each other with a tube being interposed therebetween. By using a pair of engaged rollers having substantially the same diameter and rotating them while engaging with each other, no difference in pitch circle is not caused and slippage of tube conveying is not caused. Therefore, improvement of precision can be expected.

The tube-pressing rollers 5 used in this embodiment were rollers made of a metallic material having a diameter of 70 mm and a width of 20 mm. However, their size and material are not limited thereby and the size and material suitable for this purpose may be selected depending on the material and size of the tube to be used. For example, rollers made of synthetic rubber may be used.

Thus, a tube having a different diameter and wall thickness can be used without restriction, whereby the present invention can be applied to a wide dispension range depending on the purpose of use.

Figure 2:
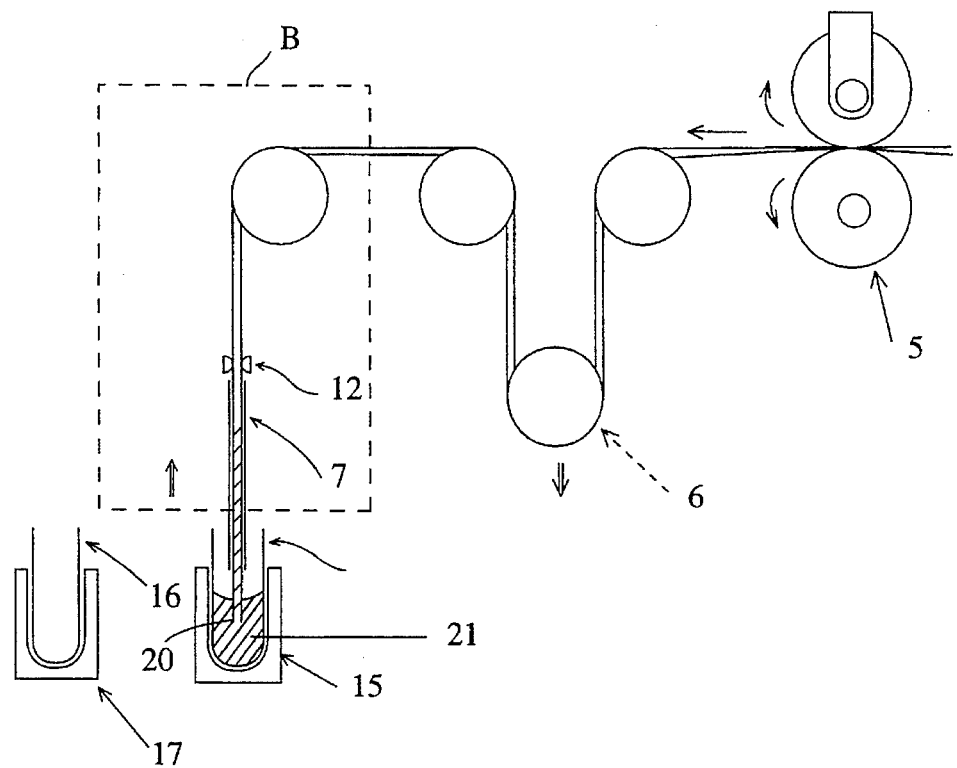
FIG. 2 is a view showing movements when a sample is sucked in the embodiment of FIG. 1 of the present invention.

The relation between the tube-pressing rollers 5 and the tube 2 is as described below. When the tube 2 is introduced between the two rollers of the tube-pressing rollers 5 and conveyed toward the nozzle 7 while being pressed as shown in FIG. 1 and FIG. 2, liquid can be sucked from a tube end 20 which comes out from the end of the nozzle 7.

Any excessive length of the tube 2 conveyed from the tube-pressing rollers 5 is absorbed by lowering the dancer roller 6, whereby a tube end position which comes out from the end of the nozzle 7 is not changed.

Then, when a liquid is to be discharged, the tube-pressing rollers 5 are rotated in the reverse direction to pull back the tube 2 toward the tube-feeding portion A.

The upper and lower two rollers of the tube-pressing rollers 5 are driven by a driving device 13 so that the rollers are rotated in a reverse direction with respect to each other. The upper roller is designed to be pressed against the lower roller with constant pressure by an air cylinder 8.

A sucking or discharging amount is controlled by the rotation number of times of the tube-pressing rollers 5.

The tube-pressing rollers 5, the dancer roller 6 and a cutting means 9 and drawing-out rollers 11 provided in the tube end-discarding portion D are fixed to the main body of the apparatus. The whole tube nozzle portion B in which the nozzle 7 and a tube holder 12 are provided can be moved to any desired position, i.e. up and down and from side to side by a driving portion not shown in the figure and constitutes a moving frame.

The cutting means 9 and the drawing-out rollers 11 may be provided in the tube nozzle portion B so that they can be moved integrally therewith.

In this example, the tube nozzle portion B is moved to a position above a sample rack 15 in which a liquid container 14 charged with a sample is put, the nozzle 7 is lowered, the tube end 20 is inserted into a sample 21 and then the sample 21 is sucked out of the container 14.

When the liquid surface of the sample 21 is not constant, before the tube end 20 is inserted, the nozzle-lowering distance may be controlled by measuring a distance to the liquid surface by, for example, an ultrasonic sensor. The drawing-out rollers 11 may be designed to sandwich the tube 2 and draw it out downwardly.

Next, movements of the dispensing apparatus of the present invention are described.

As shown in FIG. 2, the tube end 20 which comes out from the end of the nozzle 7 is inserted into a liquid (e.g. serum) in the liquid container 14 put in the sample rack 15.

The role of the tube holder 12 is not to hold the tube 2 tightly so as to be choked, but to hold the tube 2 in order to prevent the tube 2 from being pulled back from the nozzle 7 due to a weight of the dancer roller 6.

Then, the tube-pressing rollers 5 are rotated to a sucking side with a desired sucking set amount based on instructions from a pressing amount-setting means 22. The tube 2 is conveyed leftward in FIG. 2.

The tube 2 made of an elastic material is recovered by releasing a pressed portion sandwiched by the tube-pressing rollers 5 by moving it leftward successively, whereby the pressure of an inner portion of the tube 2 is reduced so as to be able to suck a serum.

Then, the tube nozzle portion B is lifted and moved to be positioned over a rack 17 in which a container 16 into which a sample is to be dispensed is located and then lowered so that the tube end 20 enters into the container 16.

Then, the tube-pressing rollers 5 are rotated to a discharging side with a desired discharging set amount based on instructions from the pressing amount-setting means 22. That is, the tube 2 is conveyed in a rightward direction in FIG. 3. A tube portion at the left side of the tube-pressing rollers 5 is squeezed, whereby a desired amount of a liquid is discharged from the tube end 20. If further dispension is required, the tube nozzle portion B is lifted, moved to upper another dispension vessel not shown in the figure and then lowered so that the tube end 20 enters into the vessel.

Then, the tube-pressing rollers 5 are rotated from the former position to a discharging side with a discharging set amount based on instructions from the pressing amount-setting means 22.

Further, if additional dispensing is required, the same movements may be repeated depending on the number of times necessary for dispension.

Figure 4:
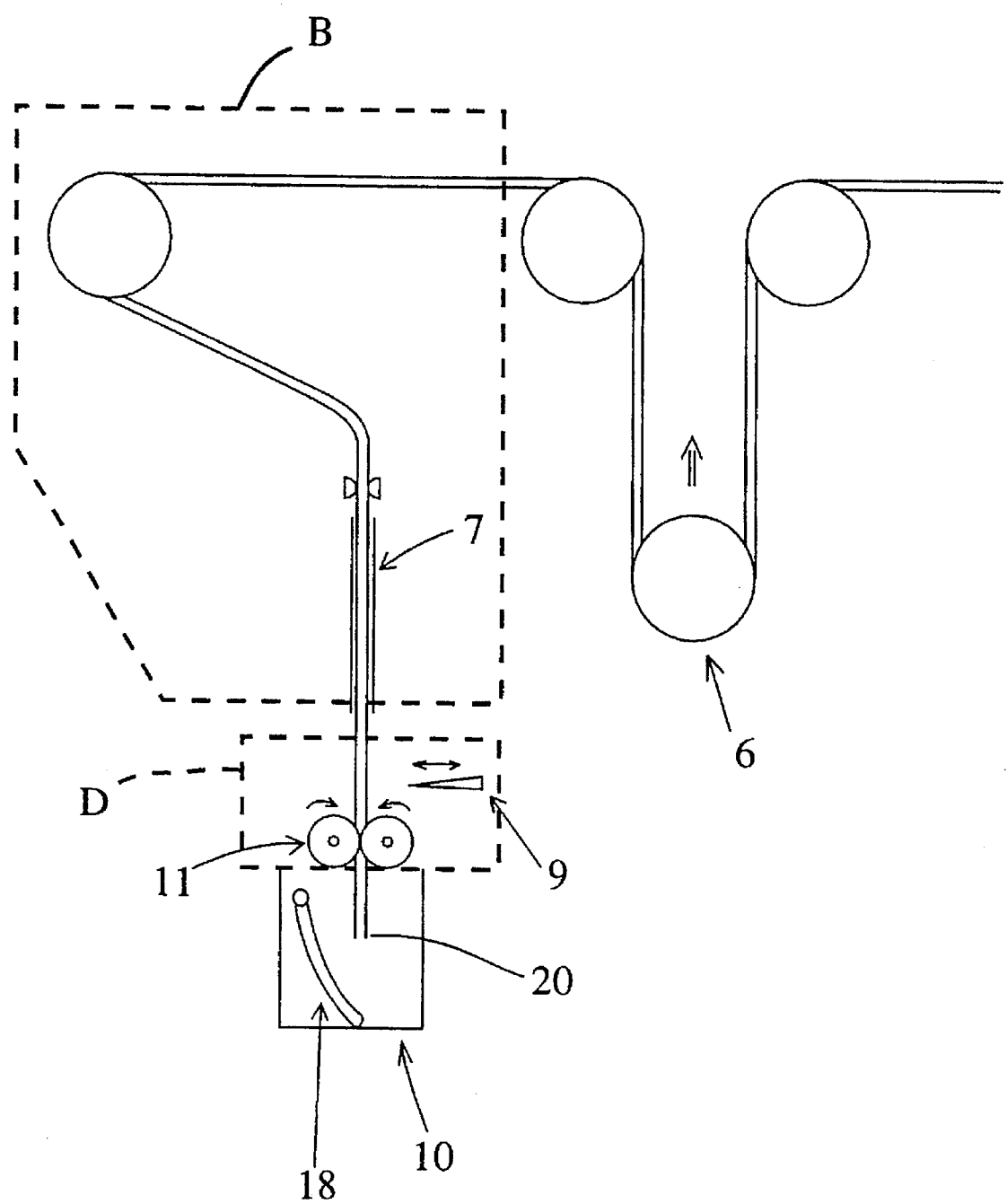
FIG. 4 is a view showing movements when a tube end is discarded in the present invention.
Figure 5:
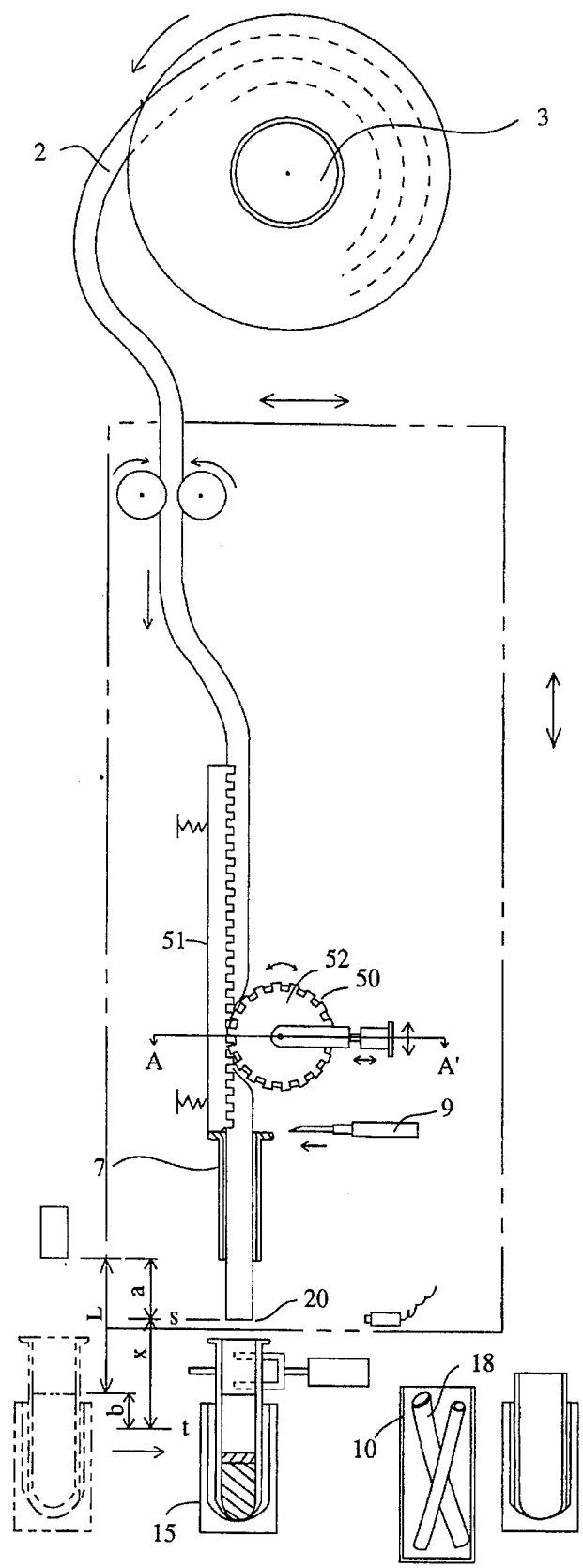
FIG. 5 is a view showing a partially improved apparatus of conventional apparatus.
Figure 6:
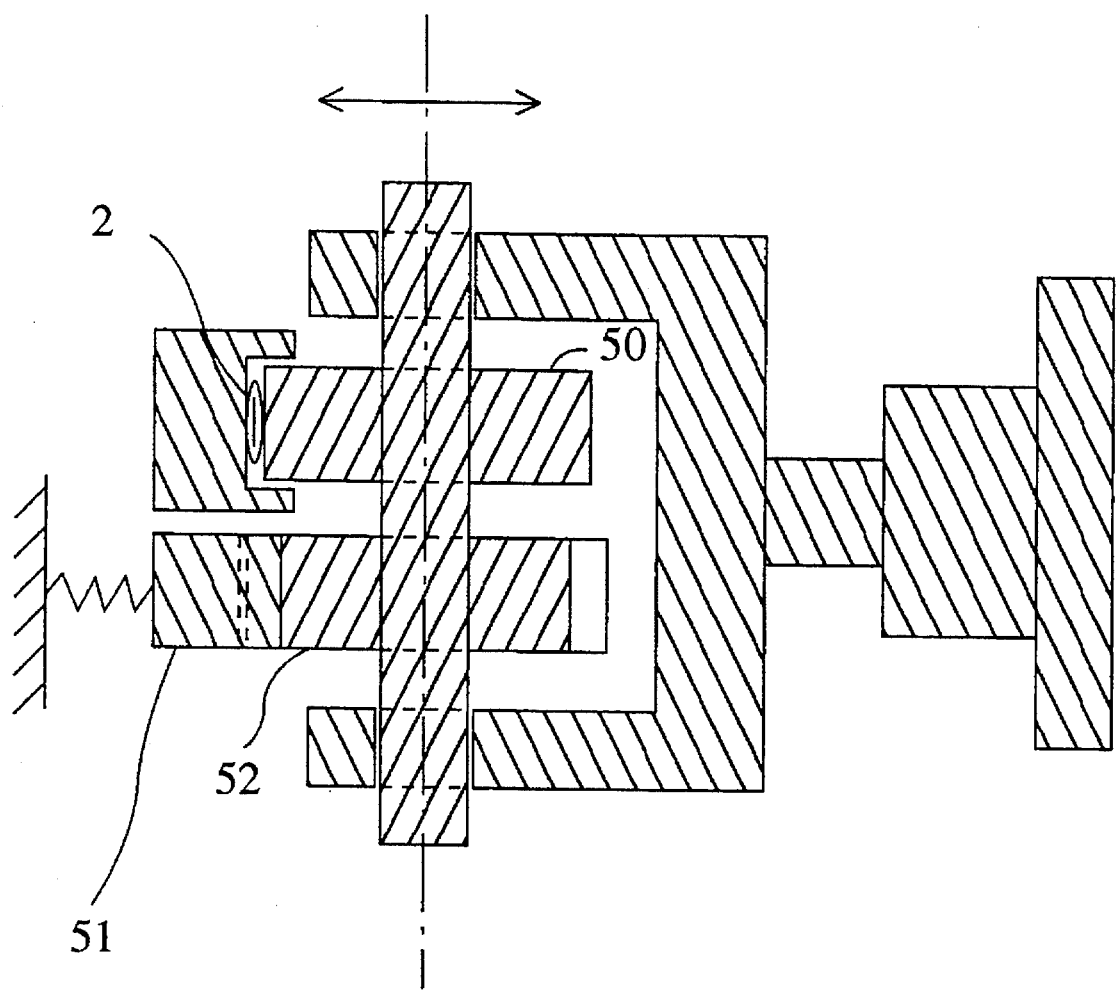
FIG. 6 is a sectional view of a pressing roller portion taken along A–A' of FIG. 5.
Figure 2:
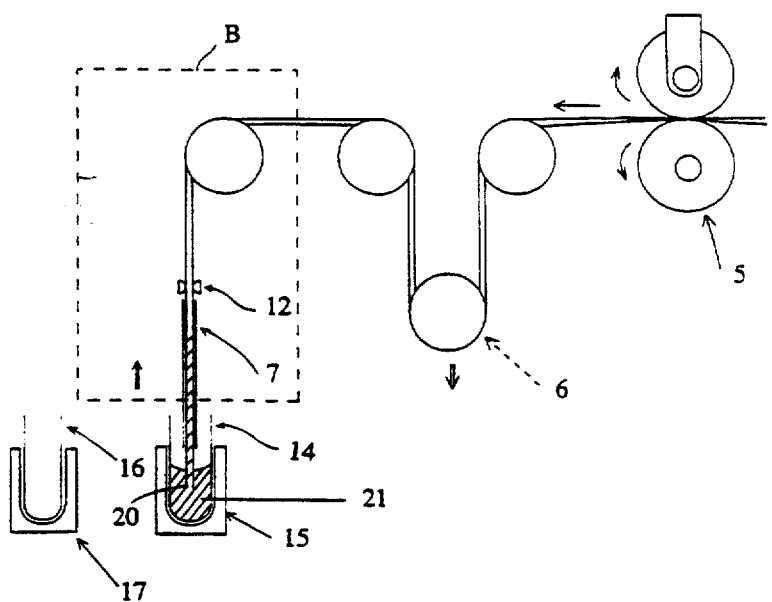
Figure 3:
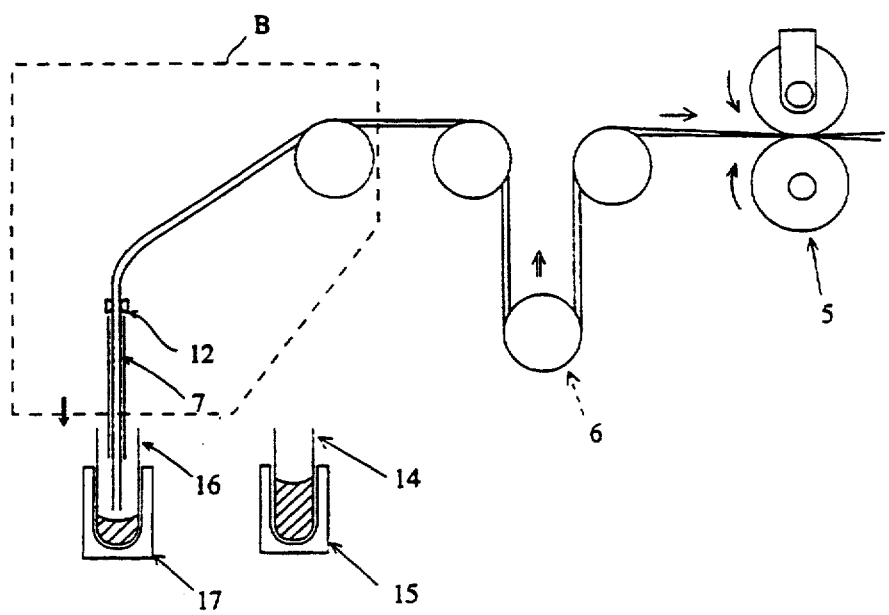

After all operations for dispensing a liquid to a dispension vessel(s) are completed, the tube nozzle portion B is moved to be positioned over a discarded tube container 10 provided in the tube end-discarding portion D as shown in FIG. 4. After a predetermined length of the tube end 20 is drawn out by the drawing-out rollers 11, the tube 2 is cut by the cutting means 9 so that the length of the tube 2 which comes out from the nozzle 7 is constant.

Then, the drawing-out rollers 11 are rotated so that a cut end of the tube (a discarded tube 18) falls into the discarded tube container 10.

Then, the tube nozzle portion B is lifted and moved to a position over a sample to be dispensed next to complete one cycle.

The effects of the invention are as follows.

1. In a conventional roller system which has been used as a sample-sucking mechanism, rotation of a pressing roller is driven by a rack and pinion system, whereby the thickness of a pressed tube causes a difference in pitch circle and the tube slightly slips when the pressing roller moves while pressing the tube so as to create an adverse influence with respect to the desired precision of operation. Further, for this reason, a tube having a different wall thickness cannot be used. These problems can be solved with the present invention. That is, in the roller system of the present invention, a pair of rollers having substantially the same diameter rotate while engaging each other so that a difference in a pitch circle is not caused and the tube does not slip, whereby dispensing precision is improved as compared with the prior art. Further, a tube having a different wall thickness can be also used so that a tube having a different tube diameter can be used, whereby the present invention can be applied to a wide dispension range depending on the purpose of use.

2. The tube-pressing and conveying portion C comprises a pair of engaged rollers which serve both as a tube-pressing member and a tube-conveying member, whereby the structure of the dispensing apparatus is simplified.

In particular, a mechanism which has been conventionally required in order to control a tube-pressing portion set amount is not required to be provided so that the dispensing apparatus can be easily miniaturized.

Also, no moving portion of a tube-choking mechanism is required so that the mechanism is simplified and also a large-sized apparatus is not required, which is economical. In the prior art, depending on a length of a moving portion, the upper limit of a dispensing amount is limited, but according to the system of the present invention, any desired amount can be dispensed without changing a mechanism size.

3. In the prior art, a tube-cutting means is provided in a tube nozzle portion, whereby movement is slow due to its heavy weight, but in the apparatus of the present invention, a tube-cutting means can be separately provided, whereby a moving portion can be lightened so as to make movement faster.

We claim:

1. A dispensing apparatus which comprises:

a tube-feeding portion which holds and feeds a tube made of an elastic material, a tube nozzle portion which supports an end portion of the tube and guides the tube to a liquid container by moving the tube up and down and from side to side, a tube-pressing and conveying portion provided between the tube-feeding portion and the tube nozzle portion, which selectively draws out the tube from the tube-feeding portion, presses the tube and conveys the tube to the tube nozzle portion and a tube end-discarding portion, wherein the tube-pressing and conveying portion comprises tube-pressing rollers which press the tube and set a length of a tube-pressing portion and wherein the tube-pressing and conveying portion comprises a dancer roller positioned between the tube feeding portion and the tube-pressing rollers, said dancer roller maintaining tension of the tubes.

2. The apparatus according to claim 1, wherein the tube-pressing and conveying portion comprises a pressing amount-setter which changes a tube-pressing portion set amount by the tube-pressing rollers in response to a control signal.

3. The apparatus according to claim 1, wherein tube-pressing rollers comprise a pair of engaged rollers having substantially the same diameter.

4. A dispensing apparatus which comprises:

a tube-feeding portion which holds and feeds a tube made of an elastic material, a tube nozzle portion which supports an end portion of the tube and guides the tube to a liquid container by moving the tube up and down and from side to side, a tube-pressing and conveying portion provided between the tube-feeding portion and the tube nozzle portion, which draws out the tube from the tube-feeding portion, presses the tube and conveys the tube to the tube nozzle portion, and a tube end-discarding portion wherein the tube-pressing and conveying portion comprises tube-pressing rollers which press the tube and set a length of a tube-pressing portion and wherein the tube-pressing and conveying portion comprises at least one dancer roller and wherein the roller absorbs a change of tube-conveying length by changing a tube-supporting position of the roller so as not to change a tube end position in the tube nozzle portion when a tube-pressing portion set amount is changed by the tube-pressing rollers.

5. The apparatus according to claim 4, wherein the tube-pressing and conveying portion comprises a pressing amount-setter which changes a tube-pressing portion set amount by the tube-pressing rollers in response to a control signal.

6. The apparatus according to claim 4, wherein the tube-pressing rollers comprise a pair of engaged rollers having substantially the same diameter.

* * * * *

UNITED STATES PATENT AND TRADEMARK OFFICE
CERTIFICATE OF CORRECTION

Figure 3:
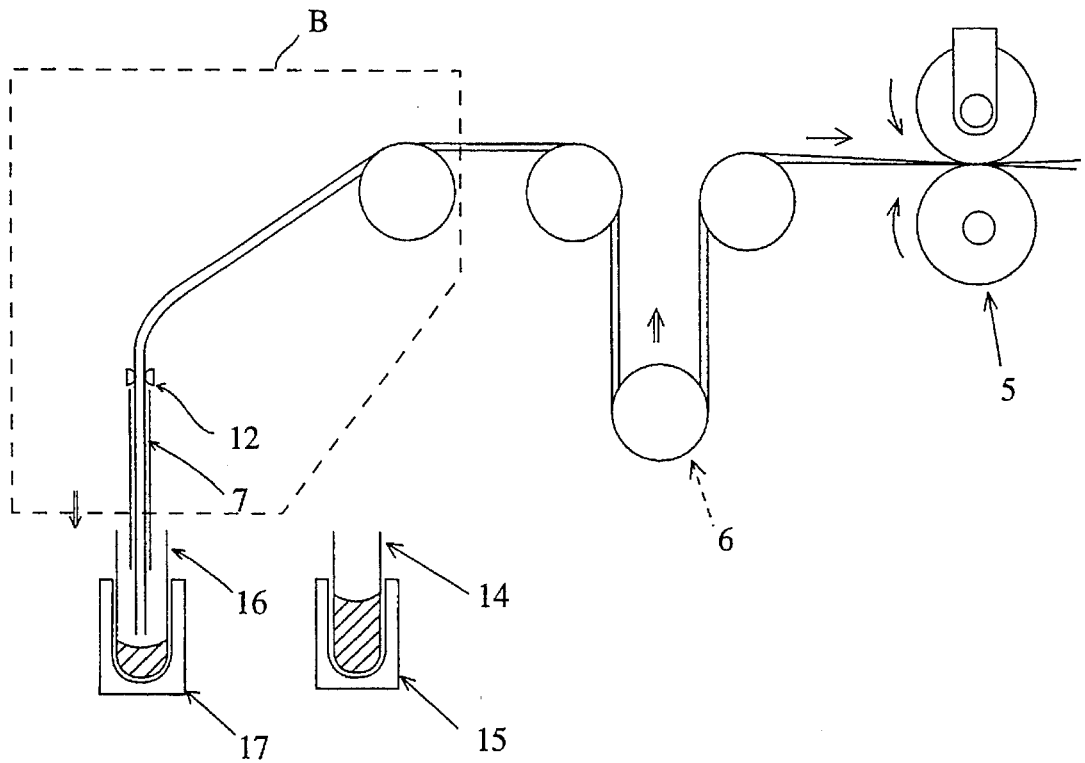
FIG. 3 is a view showing movements when a sample is discharged in the present invention.

PATENT NO. : 5,453,246  Page 1 of 2
DATED : SEPTEMBER 26, 1995
INVENTOR(S) : Naoki NAKAYAMA ET AL It is certified that error appears in the above-indentified patent and that said Letters Patent is hereby corrected as shown below:

Delete drawing sheet 2 of 5, and substitute therefor the drawing sheet, consisting of Figs. 2 and 3, as shown on the attached page.

Signed and Sealed this

Twenty-sixth Day of March, 1996

Attest:

BRUCE LEHMAN

Attesting Officer    Commissioner of Patents and Trademarks